United States Patent [19]
Jettka et al.

[11] Patent Number: 6,024,987
[45] Date of Patent: *Feb. 15, 2000

[54] PHARMACEUTICAL, ORALLY APPLICABLE COMPOSITION

[75] Inventors: Winfried Jettka; Benedikt Gajdos, both of Köln; Manfred Dürr, Bergheim-Glessen, all of Germany

[73] Assignee: Rhone-Poulenc Rorer GmbH, Cologne, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/566,825

[22] Filed: Dec. 4, 1995

[30] Foreign Application Priority Data

Dec. 10, 1994 [DE] Germany ............................ 44 44 052

[51] Int. Cl.⁷ .......................... A61K 33/06; A61K 31/34; A61K 31/195
[52] U.S. Cl. ........................... 424/682; 514/461; 514/561
[58] Field of Search ..................................... 514/461, 561; 424/682

[56] References Cited

FOREIGN PATENT DOCUMENTS

| 0 600 725 A1 | 6/1994 | European Pat. Off. . |
| 0 636 365 A1 | 2/1995 | European Pat. Off. . |
| 749285 | 5/1956 | United Kingdom . |

OTHER PUBLICATIONS

Chemical Abstracts 121:91841 (1994). Roche et al.

*Primary Examiner*—Zohreh Fay
*Attorney, Agent, or Firm*—Proskauer Rose LLP

[57] ABSTRACT

A pharmaceutical, orally applicable composition is described, whereby the solid composition contains at least one antacid active ingredient and/or at least one $H_2$-antagonist, at least one disintegrant, as well as at least one usual pharmaceutical additional ingredient. Furthermore said composition contains at least one ingredient that accelerates the decomposition of said composition in the mouth or in a liquid, whereby said ingredient is a water-soluble amino acid, a water-soluble amino acid derivative and/or a water-soluble amino acid salt.

14 Claims, No Drawings

PHARMACEUTICAL, ORALLY APPLICABLE COMPOSITION

The present invention concerns a pharmaceutical, orally applicable composition with the characteristics of the generic part of the main claim.

Solid, orally applicable pharmaceutical compositions that contain at least one antacid active ingredient and/or one $H_2$-antagonist, at least one disintegrant, as well as at least one pharmaceutically usual additional ingredient, are known for a long time and available on the trade market. Depending on the respective active ingredient and/or the active ingredient mixture, said known antacids are used as tablets, coated tablet or powder in order to prevent and/or to treat stomach troubles, especially for the treatment of nausea, stomach cramps, heartburn, bloating, acid eructations, vomiting, flatulence, gastric ulcer and/or pains after alcohol-abusing and/or nicotine-abusing. In general therefore is required that the patient swallows the corresponding tablet or coated tablet chewed, which often leads to a conglutination of components of said tablet and/or coated tablet in the dental and/or palatal area of the mouth. The removal of said conglutinated components causes problems and furthermore releases the active ingredient in the course of time, which after all then causes a very unpleasant taste in the mouth.

In order to avoid the above described problems with the application of said known pharmaceutical compositions, specifically produced tablets are known that inevitably decompose relatively fast in the mouth or in a corresponding liquid, so that hereby the chewing in the mouth of said known tablets that usually is also named Lyoc-tablets, can be omitted. Such specific and known pharmaceutical compositions have however the handicap that they can be slightly and undesirably damaged while being produced, while being transported or while being applied to the patient, so that also their use is correspondingly limited.

The aim of the present invention is to make disposable such an orally applicable, solid composition that on one side shows a particular high stability and on the other side decomposes very fast while being applied.

Said aim is realized, according to the invention, by a pharmaceutical composition with the distinguishing features of the patent claim 1.

The inventive pharmaceutical and orally applicable solid composition, contains at least one antacid active ingredient and/or at least one $H_2$-antagonist, at least one disintegrant, as well as at least one pharmaceutically usual additional ingredient. Furthermore said inventive composition contains at least one ingredient that accelerates the decomposition of said composition in the mouth or in a liquid, whereby said ingredient is a water-soluble amino acid, a water-soluble amino acid derivative and/or a water-soluble salt of an amino acid.

Surprisingly it was observed that said composition shows a very high decomposition rate, caused by the above indicated at least one ingredient (water-soluble amino acid, water-soluble amino acid derivative and/or a water-soluble salt of an amino acid), which means that, relatively to the time, said composition shows a high decomposition when it gets in contact with saliva (spittle) or an appropriate liquid, especially water. This again leads to a very fast decomposition (disintegration) of said inventive composition in the mouth, without being required to chew said inventive composition. Therefore there are no problems concerning said inventive composition, as there are known in connection with the compositions (according to the prior art) and also incorporate with such known compositions that contain a disintegrant. That means that the components of said inventive composition do not deposit in areas of the mouth that are difficult to reach and therefore do not cause an unwanted conglutination on the tongue and/or on the palate and/or in the dental area, so that correspondingly said inventive composition does not cause a bitter taste during the application of said composition in the patient's mouth, caused by the release of the active ingredient. Furthermore the above mentioned ingredient (water-soluble amino acid, water-soluble amino acid derivative and/or a water-soluble salt of an amino acid) accelerating the decomposition of said inventive composition in the mouth or in a liquid, does not deteriorate the stability of said composition, so that also said inventive composition is not undesirably damaged during its production, transport and application, so that correspondingly the complaint rate regarding said inventive compositions particularly low. Also said inventive composition can be manufactured particularly low-priced by conventional manufacturing techniques, while contrarily this is not the case concerning the known and above mentioned Lyoc manufactured-tablet.

The above indicated high decomposition rate of the inventive composition is referred to a synergistic effect of the at least one disintegrant with the ingredient (water-soluble amino acid, water-soluble amino acid derivative and/or water-soluble salt of an amino acid).

Basically the inventive composition can contain each water-soluble amino acid, each water-soluble amino acid derivative and/or each water-soluble salt of an amino acid, if it is secured that the above indicated ingredients that accelerate the decomposition of said inventive composition in the mouth and/or in a liquid, are not toxic, and do not show interaction with the at least one antacid active ingredient and/or the at least one $H_2$-antagonist. It is particularly suitable, if the inventive composition contains the ingredient glycine, glycine derivative and/or a salt of glycine, that accelerate the decomposition of said inventive composition, whereby the term glycine derivative includes particularly ester, preferably of $C_1$–$C_4$-alcohols and/or amides of glycine, preferably of $C_1$–$C_{10}$-carboxylic acids, and the term salts of glycine includes preferably water-soluble alkalisalts and/or alkaline earth salts, as well as the corresponding ammonium salts. These above described embodiments of the inventive composition that contain as ingredient glycine, a glycine derivative, a salt of glycine and/or their mixture, are toxicologically seen absolutely unobjectionable, whereby, caused by the relatively low price of the above indicated ingredients basing on glycine, the embodiment of the inventive composition is manufacturable to a particular low price.

Another embodiment of the inventive pharmaceutical composition contains such ingredients accelerating the decomposition (disintegration) of the inventive composition, additionally to above described ingredients basing on glycine, or instead of the ingredients basing on glycine. Said accelerating ingredients are chosen from the group consisting in proline, hydroxy proline, lysine, the salts thereof and/or derivatives thereof. Hereby the term salts and the term derivatives include the salts and derivatives indicated above together with the glycine, whereby however concerning the proline, respectively the hydroxy proline it is possible to correspondingly substitute the pyrrolidine-ring, particularly to halogenate it and/or to provide at the pyrrolidine-ring an additional $NH_2$-group, a $NO_2$-group and/or a $SO_3H$-group. Also one or more of the above mentioned substitutes can be arranged at the non-substituted $CH_2$-groups of the lysine.

Concerning the previous and exactly described ingredients of the inventive composition that accelerate the decomposition of the inventive composition in the mouth and/or in a liquid, it is to be noted that the inventive composition contains the ingredients in such a concentration that the composition decomposes (disintegrates) in the mouth, respectively in a chosen liquid within one second up to sixty seconds, preferably within one second up to thirty seconds.

Depending on each antacid active ingredient and/or $H_2$-antagonist and on the usual additional ingredients, as well as on the composing of said composition, the concentration of the ingredient, respectively of the ingredient-mixture varies in said composition between 1% by weight and 90% by weight, preferably between 20% by weight and 70% by weight, corresponding to the composition ready to use.

As disintegrants the inventive composition contains preferably starch, a starch derivative, cellulose, a cellulose derivative, alginic acid, an alginic acid derivative, casein, a casein derivative and/or a water-insoluble polyvinylpyrrolidone (crosspolyvidone). The above mentioned starch is particularly a corn- or a potato starch, the above mentioned starch derivative is particularly modified starch and/or sodium carboxymethyl starch, also in a cross-linked form, the above mentioned cellulose derivative is particularly carboxymethyl cellulose and/or calcium-and/or sodium carboxymethyl cellulose, also in a cross-linked form. Furthermore, appropriate disintegrants are cross-linked casein, sodium salt of alginic acid, as well as polyvinylpyrrolidone (cross-linked) insoluble in saliva and/or water, whereby the latter mentioned product is also available on the market under the trade name Kollidon CL and Polyplasdone XL.

Concerning the concentration of the disintegrant in the inventive composition it is to be noted that it varies between 1% by weight and 50% by weight, preferably between 3% by weight and 20% by weight, corresponding to the composition ready to use (apply).

A especially favorable further development of the above described embodiment of the inventive composition provides that hereby the inventive composition contains the at least one antacid active ingredient in the form of active ingredient particles that are proportionately dispersed in the solid composition. Especially when the antacid active ingredients and/or particles of said $H_2$-antagonist have a size of between 10 µm and 1.000 µm, preferably between 50 µm and 400 µm, then such a further development of said composition has next to a perfect stability, next to a particularly fast decomposition rate, also a specifically high efficacy. One reason for this is that after the decomposition of the inventive composition the each active ingredient particle reaching the stomach, has a relatively large surface, so that they can cause correspondingly fast the desired therapeutic effects.

Concerning the antacid active ingredient, respectively the antacid active ingredient mixture of the inventive composition it is to be noted that they are the known antacid active ingredients, preferably aluminium-hydroxide, magnesium-hydroxide, magnesium-trisilicate, magnesium-carbonate, magnesium-phosphate, calcium-carbonate, calcium-phosphate, sodium-citrate, magnesium-oxide, magaldrate, hydrotalcite, $(Al_2Mg_6(CO_3)(OH)_{16} \times 4H_2O)$) sodium-hydrogenecarbonate and/or bismuth-subcarbonate.

Concerning the concentration of the antacid active ingredients of the inventive composition is to be noted that this concentration of the active ingredient, respectively of the active ingredient mixture varies between 1% by weight and 70% by weight, preferably between 15% by weight and 60% by weight, each corresponding to said composition ready to use.

Especially then, when the inventive composition contains as an active ingredient a hydrophilic antacid active ingredient and/or a hydrophilic $H_2$-antagonist, it is recommendable to provide said hydrophilic active ingredient with a hydrophobic coating-layer and/or to embed said hydrophilic active ingredient into a hydrophobic matrix. This embodiment of the inventive composition does not only show the already previous mentioned advantages (high decomposition rate, sufficient hardness and resistance), but also is characterized in that during the decomposition of the inventive composition in the mouth the active ingredient, respectively the concrete active ingredient particles is and/or are prevented from forming large agglomerates by the hydrophobic coating-layer and/or the hydrophobic matrix, which would avoid the desired fine dispersion of the active ingredient. Furthermore, by such a hydrophobic coating-layer and/or hydrophobic matrix is achieved that a bitter or unpleasant taste possibly caused by the active ingredient is suppressed.

The above mentioned suppression of the bitter and/or unpleasant taste of said active ingredient by maintaining a particularly short decomposition time, can also be achieved for the reason that the inventive composition contains an active ingredient and/or an active ingredient mixture that is not provided with hydrophobic coating-layer and/or embedded into a hydrophobic matrix, but instead contains larger, previously consolidated active ingredient particles or active ingredient particles granulated to a corresponding particle size. Herewith such consolidated and/or granulated active ingredient particles are meant that represent a mixture of said active ingredient with an inactive ingredient, particularly with a sugar and/or a sugar-alcohol. By such a consolidation and/or granulation, specifically by a compression, of the active ingredient particles to larger agglomerates, the disposable surface is decreased in comparison to the actual, small active ingredient particles, so that correspondingly the decomposition procedure of said actual active ingredient, but not of the solid compound as a whole, in the mouth is delayed, which again suppresses an unpleasant or bitter taste.

For the above mentioned coating and/or embedding of said active ingredient and/or said active ingredient mixture in a hydrophobic matrix, basically all coating substances and/or embedding substances can be chosen, that on one side secure the unwanted hydrophobization of the active ingredient and/or the active ingredient mixture and on the other side are toxicologically unobjectionable. Heretofore especially coating-layers and/or embedding substances are considered that are chosen from the group consisting of shellac, stearic acid, gelatine, zein, gum arabic, cellulose derivatives, polymere acrylic acid derivatives and/or polymere vinylacetates. To be mentioned concretely are methylcellulose, ethylcellulose, hydroxypropylcellulose, hydroxypropylmethylcellulose, celluloseacetate-phthalate, hydroxypropylmethylcellulose-phthalate, as well as polymere acrylic acid derivatives, particularly copolymerisates from methacrylic acids and esters from methacrylic acids; acrylic acid ethyl-methacrylic acid methylester-copolymerisates; methacrylic acid-acrylic acid methylester-copolymerisates; acrylic-and methacrylic acid ester-copolymerisates with trimethylammoniummethacrylate; copolymerisate from dimethylaminomethacrylic acid and neutral methacrylic acid esters; vinylpyrrolidone-vinylacetate-copolymerisates; polyvinylacetate; polyvinylpyrrolidone as well as polyethylenglycol.

Concerning the amount of the above mentioned coating- and/or embedding substances it is to be noted that this amount of said coating- and/or embedding substances depends on the concentration of the corresponding hydrophilic active ingredient and/or the hydrophilic active ingredient mixture. The amount of said substances varies between 1% by weight and 10% by weight corresponding to the inventive composition ready to use.

A further development of the above described embodiment of the inventive composition shows preferably instead of the at least one antacid active ingredient at least one $H_2$-antagonist, particularly cimetidine, famotidine, ranitidine and/or nizatidine. Hereby the concentration of the above mentioned $H_2$-antagonist varies between 1% by weight and 75% by weight, preferably between 5% by weight and 50% by weight, each corresponding to the inventive composition ready to use.

Especially a combination of antacid active ingredient and/or antacid active ingredient mixture and the above mentioned $H_2$-antagonists has perfect prophylactic and/or therapeutical characteristics and can be used specifically for the treatment of ulcer affections of the stomach and/or of the duodenum, as well as of reflux oesophagitis.

Furthermore the inventive composition contains pharmaceutically usual additional ingredients, which are in particular bulkages, binders, lubricants, humectants, absorbents, antistatic substances, colouring substances, preservatives and flavouring substances.

In particular the inventive composition contains pharmaceutically usual bulkages and binders, in a concentration between 0% by weight and 60% by weight. Further it contains polyvinylpyrrolidone, propylenglycol, polyethylenglycol, sugar, sugar alcohols, xanthan gum and/or guar gum, each in a concentration between 0% by weight and 10% by weight, as well as an usual concentration of flavouring substances, particularly sweetening substances and/or aromatics.

As already previous mentioned the inventive pharmaceutical composition is solid and exists preferably as a tablet or granular powder. However, it is of course possible to manufacture the inventive composition in the form of a relatively coarse-grained powder.

Further favorable developments of the inventive composition are indicated in the sub-claims.

The inventive composition is explained more precisely in the examples.

Hereinafter in the examples the terms consolidation, spray-drying, hydro-granulation are used.

By the term consolidation a procedure is meant in which the active ingredient and/or the active ingredient mixture is consolidated with a concrete additional ingredient and/or additional ingredient mixture mentioned in the examples, possibly by the addition of water, with an appropriate device, specifically a consolidating roller or a tablet compressor. Thereafter the concreted material is crushed and if necessary dried. Should the portion of fine grains in the said concreted material be to high, particularly under 80 μm, then said portion can be removed by being sieved.

By the term spray-drying a procedure is meant in which the active ingredient and/or the active ingredient mixture is dissolved or dispersed in water. Hereby the additional ingredients mentioned concretely in the examples, are added. Thereafter the dispersion and/or solution is dried in a spray tower in a stream of warm air with a product temperature between 30° C. and 120° C.

By the term hydrogranulation a procedure is meant in which the active ingredient and/or the active ingredient mixture is granulated in an appropriate device, particularly in a mixer and/or a fluid bed granulator, during addition of the additional ingredients mentioned in the examples. Depending on the chosen active ingredient and the additional active ingredients the granular powder can be coated with an appropriate polymer.

When the products, submitted to the spray-drying, the hydrogranulation and the consolidation, are coated with an appropriate polymer which is in the following examples the product Eudragit E12,5, then this is marked in the following quoted examples by indicating the above mentioned product.

For the following components named in the examples with their trade names, Kollidon CL (BASF), Aerosil 200 (Degussa), Acesulfam K (Hoechst), and Eudragit E 12,5 (R öhm) the manufacturers are indicated in brackets after each component.

EXAMPLE 1

Manufacturing of an aluminium-hydroxide/magnesium-hydroxide-containing tablet
A mixture containing

| - 5.714 kg | water-containing aluminium-oxide * |
| - 5.714 kg | magnesium-hydroxide powder, anhydrous; |
| - 2.071 kg | sorbitol solution 70% by weight (not crist.) and |
| q.s. | water | is correspondent to 2.857 kg $Al_2O_3$ (anhydrous) q.s. means the quantity of water that is required in order to adjust the right water content of the powder mixture for the consolidation (ca. 10–15% by weight).

was first of all manufactured by an intensive mixing. After this mixture was consolidated (concreted) the concreted material was crushed and dried. The hereby emerging intermediate was mixed with the following components 5.357 kg glycine, 1.228 kg Kollidon CL (cross-linked povidone), 95 g Aerosil 200, 16 g Acesulfam K, 61 g aromatics 261 g talcum and 12 g magnesium stearate and the thereby emerging homogeneous mixture was compressed to tablets weighing 1,400 mg. The compression power totaled 30 kN (=kilo Newton) with a tablet diameter of 16 mm.

EXAMPLE 2

Manufacturing of an aluminium-hydroxide/magnesium-hydroxide-containing tablet
A mixture containing 1,250 g aluminium-hydroxide-gel *, 1,000 g magnesium-hydroxide-paste, 543 g sorbitol, 70%, not cristallised, 13.8 g povidone and 1.8 g saccharine sodium is correspondent to 200 g $Al_2O_3$ (anhydrous).

was submitted to a spray-drying with a temperature of 108° C. The product that emerged from the spray-drying was coated with 36 g Eudragit E 12,5 and thereafter it was mixed thoroughly with the following components 1,200 g glycine,
240 g Kollidon CL (cross-linked povidone),
10 g Aerosil 200,
6 g aromatics,
50 g talcum and
24 g magnesium stearate.

The homogeneous mixture, hereby emerging, was compressed to tablets weighing 1,380 mg and having a diameter of 16 mm with a compression power of 35 kN.

EXAMPLE 3

Manufacturing of an aluminium-hydroxide/magnesium-hydroxide-containing tablet
A mixture containing
    800 g water containing aluminium-oxide *,
    800 g magnesium-hydroxide powder, anhydrous,
    290 g saccharose,
    300 g mannitol,
    98 g sorbitol, 70%, not cristallising and
    9 g saccharine sodium
* is correspondent to 400 g $Al_2O_3$ (anhydrous)

was manufactured by a hydrogranulation. Thereafter the granular powder was dried and coated with
    50 g Eudragit E 12,5.
To the coated granular powder the following components were added
    1,200 g glycine
    240 g Kollidon CL,
    10 g Aerosil 200,
    6 g aromatics,
    56 g talcum and
    14 g magnesium stearate.

The homogeneous mixture was compressed to tablets weighing 1,963 mg and having a diameter of 17.5 mm with a compression power of 40 kN.

EXAMPLE 4

Manufacturing of a magaldrate-containing tablet
A mixture containing
    800 g magaldrate and
    143 g sorbitol solution 70% by weight (not cristallising)
was manufactured. Thereafter this mixture was consolidated by a roller. The consolidated mixture was crushed, dried and then mixed with the following components
    375 g glycine,
    100 g Kollidon CL,
    6.7 g Aerosil 200,
    1.1 g Acesulfam K
    4.3 g aromatics,
    18.3 g talcum and
    8.6 g magnesium stearate.

The homogeneous mixture was compressed to tablets weighing 1,415 mg and having a diameter of 16 mm with a compression power of 30 kN.

EXAMPLE 5

Manufacturing of a hydrotalcite-containing tablet
A mixture containing
    1,000 g hydrotalcit and
    140 g xylitol
was manufactured. Thereafter this mixture was consolidated by a roller. The consolidated product was crushed and dried. To this dried product the following components were added
    400 g glycine,
    130 g Kollidon CL,
    8.3 g Aerosil 200,
    1.5 g Acesulfam K,
    5.6 g aromatics,
    20 g talcum and
    9.3 g magnesium stearate.

After the homogenisation this mixture was compressed to tablets with the weight of 1,715 mg and a diameter of 17.5 mm with a compression power of 35 kN.

EXAMPLE 6

Manufacturing of a cimetidine-containing tablet
A mixture containing
    400 g cimetidine,
    144 g sorbitol solution 70% by weight, (not cristallising) and
    9 g saccharine sodium
was manufactured. Thereafter this mixture was consolidated by a roller and granulated and dried. Thereafter the dried product was coated with
    20 g Eudragit E 12,5.
The coated product was thereafter mixed with the following components
    400 g glycine,
    80 g Kollidon CL,
    6 g Aerosil 200,
    4 g aromatics,
    20 g talcum and
    8 g magnesium stearate.

Thereafter the homogenised mixture was compressed to tablets weighing 525 mg and having a diameter of 12 mm with the compression power of 10 kN.

According to the previous indicated manufacturing instructions in the examples 1–6 further tablets I–VI were correspondingly produced, whereby said further tablets I–VI did not contain glycine. On the contrary the glycine was replaced by a quantity of sorbitol corresponding to the quantity of glycine.

Of the tablets manufactured according to the examples 1–6 and the comparison tablets I–VI that did not contain glycine, the decomposition times were measured. Heretofore a modified apparatus according to DAB 10 (German Pharmacopoeia) was used.

Said modified apparatus consisted in a rack with a sieving base comprising six cylindrical glass test-tubes. Said tubes, open at the upper end, were closed at the lower end only by stainless steel wire, so that the liquid could freely enter the tube. Said rack was constantly vertically moved up and down by a motor, whereby the speed was set that way that said rack was moved up and down 28 to 32 times per minute over a way of 55 mm to 60 mm. Hereby said rack was arranged in a 1-liter beaker, whereby said beaker was filled with 350 ml of cleaned water. Said rack was positioned that way that said tubes had left the water by reaching the extreme point of the upward movement, and by reaching the extreme point of the downward movement they had immersed in the water that deep that all tablets arranged in said tubes were wetted completely.

In each tube one tablet was arranged.

The temperature of the water was set during the measurement on a level between 36° C. and 38° C.

Then said rack was moved up and down that long till all tablets to be tested were decomposed. The decomposition time heretofore required was measured, whereby in the following table 1 the uppermost and the lowest decomposition time determined by six measurements are indicated.

TABLE 1

Decomposition times of the tablets manufactured according to the examples 1–6 as well as of the tablets I–VI (without the addition of glycine)

| tablet according to example | decomposition time in seconds |
|---|---|
| 1 | 10 |
| 2 | 18 |
| 3 | 20 |
| 4 | 15 |
| 5 | 15 |
| 6 | 12 |
| referent tablets | |
| I | = 300 |
| II | = 300 |
| III | = 300 |
| IV | = 300 |
| V | = 300 |
| VI | = 300 |

A taste- and acceptance-test was made with 30 persons who for several days took a trade-usual tablet according to III or an externally identical tablet-shaped remedy (according to example 3) that differed from the known remedy in the way that it contained additionally the quantity of glycine indicated in example 3.

The persons could not distinguish both tablets from their exterior. Each person received the trade-usual tablet, as well as the above mentioned tablet-shaped remedy.

All the 30 persons conformably reported how pleasant and easy the use of the tablet mixed with glycine (according to example 3) was.

In particular the probationers conformably confirmed that compared to the conventional antacid, the tablet mixed with glycine was regarded as extremely positive and pleasant during the use and chewing in the mouth. The typical and permanent conglutination of the known tablet and its components on the palate, teeth and gums was not observed during the application and use of the tablet mixed with glycine. Also this tablet dissolved a lot faster which was considered as very comfortable.

We claim:

1. A pharmaceutical, orally applicable solid composition wherein the solid composition contains at least one antacid active ingredient, or at least one $H_2$-antagonist, or mixtures thereof, at least one disintegrant selected from the group consisting of starch, a starch derivative, cellulose, a cellulose derivative, alginic acid, an alginic acid derivative, casein, a casein derivative, an insoluble ipolyvinylpyrrolidone, and mixtures thereof, at least one usual pharmaceutical additional ingredient, and at least one ingredient accelerating the decomposition of said composition in the mouth or in a liquid, wherein said ingredient is selected from the group consisting of glycine, proline, hydroxy proline, lysine, and the salts and derivatives thereof, wherein said composition contains said ingredient in such a concentration that the composition decomposes in the mouth or in a liquid within one to thirty seconds.

2. The pharmaceutical composition according to claim 1, which contains said ingredient in a concentration between 1% by weight and 90% by weight, based on the total weight of the composition.

3. The pharmaceutical composition according to claim 1 which contains said disintegrant in a concentration between 1% by weight and 50% by weight, based on the total weight of the composition.

4. The pharmaceutical composition according to claim 1 containing at least one antacid active ingredient as active ingredient particles uniformly dispersed in said solid composition.

5. The pharmaceutical composition according to claim 2, wherein said active ingredient particles have a particle size between 10 $\mu$m and 1.000 $\mu$m.

6. The pharmaceutical composition according to claim 1, wherein the antacid active ingredient is selected from the group consisting of aluminum-hydroxide, magnesium-hydroxide, magnesium-trisilicate, magnesium-carbonate, magnesium-phosphate, calcium-carbonate, calcium-phosphate, sodium-citrate, magnesium-dioxide, magaldrate, hydrotalcite, sodium-hydrogencarbonate and bismuth-subcarbonate.

7. The pharmaceutical composition according to claim 6 wherein said composition contains the antacid active ingredient in a concentration between 1% by weight and 70% by weight, based on the total weight of the composition.

8. The pharmaceutical composition according to claim 1 wherein said composition contains at least one hydrophilic antacid active ingredient provided with a hydrophobic coating layer.

9. The pharmaceutical composition according to claim 8, wherein said hydrophobic coating layer comprises shellac, stearic acid, gelatine, zein, gum arabic, cellulose derivatives, polymeric acrylic acid derivatives, polymeric vinylacetates, and mixtures thereof.

10. The pharmaceutical composition according to claim 1 wherein said composition contains as active ingredient at least one $H_2$-antagonist selected from the group consisting of cimitidine, ranatidine and famotidine.

11. The pharmaceutical composition according to claim 10, wherein said composition contains the $H_2$-antagonist in a concentration between 1% by weight and 75% by weight, based on the total weight of the composition.

12. The pharmaceutical composition according to claim 1, wherein said solid composition contains as additional ingredients between 0% by weight and 60% by weight bulkages and binders, between 0% by weight and 10% by weight of at least one substance selected from the group consisting of polyvinylpyrrolidone, propylenglycol, polyethylenglycol, sugar, sugar alcohols, xanthan gum and guar gum, sweetening agents, aromatics, and mixtures thereof.

13. The pharmaceutical composition according to claim 1, wherein said active ingredient comprises active ingredient particles consolidated under pressure, or a particle mixture of active ingredient and at least one inactive ingredient, consolidated under pressure.

14. The pharmaceutical composition according to claim 1, wherein said composition has the form of a tablet or a granular powder.

* * * * *